US008394644B2

(12) United States Patent
Gu et al.

(10) Patent No.: US 8,394,644 B2
(45) Date of Patent: Mar. 12, 2013

(54) MICROFLUIDIC OSMOTIC PUMP

(75) Inventors: Yuandong Gu, Plymouth, MN (US);
Wei Yang, Minnetonka, MN (US);
Aravind Padmanabhan, Plymouth, MN (US)

(73) Assignee: Honeywell International Inc., Morristown, NJ (US)

( * ) Notice: Subject to any disclaimer, the term of this patent is extended or adjusted under 35 U.S.C. 154(b) by 1232 days.

(21) Appl. No.: 11/983,255

(22) Filed: Nov. 8, 2007

(65) Prior Publication Data

US 2009/0123297 A1     May 14, 2009

(51) Int. Cl.
*G01N 15/06* (2006.01)
*G01N 33/00* (2006.01)
*G01N 33/48* (2006.01)

(52) U.S. Cl. ........ 436/180; 422/502; 422/503; 422/504; 422/505; 436/174; 436/164; 436/172; 436/43; 417/1; 417/21

(58) Field of Classification Search .......... 422/502, 422/503, 504, 505; 436/174, 180, 164, 172, 436/43; 417/1, 21
See application file for complete search history.

(56) References Cited

U.S. PATENT DOCUMENTS

| | | | |
|---|---|---|---|
| 3,760,805 A | | 9/1973 | Higuchi |
| 3,865,108 A * | | 2/1975 | Hartop .................. 424/430 |
| 4,034,756 A | | 7/1977 | Higuchi et al. |
| 4,111,202 A * | | 9/1978 | Theeuwes .................. 604/892.1 |
| 4,180,073 A * | | 12/1979 | Michaels .................... 604/892.1 |
| 4,203,442 A * | | 5/1980 | Michaels .................... 604/892.1 |
| 4,320,758 A * | | 3/1982 | Eckenhoff et al. ......... 604/892.1 |
| 4,340,054 A * | | 7/1982 | Michaels .................... 604/892.1 |
| 4,595,583 A * | | 6/1986 | Eckenhoff et al. ............ 424/438 |
| 5,169,390 A | | 12/1992 | Athayde et al. |
| 5,290,240 A | | 3/1994 | Horres, Jr. |
| 7,355,277 B2 | | 4/2008 | Myers et al. |
| 7,458,783 B1 | | 12/2008 | Myers et al. |
| 2002/0100714 A1 * | | 8/2002 | Staats .......................... 210/85 |
| 2003/0232203 A1 | | 12/2003 | Mutlu et al. |
| 2005/0070884 A1 | | 3/2005 | Dionne et al. |
| 2005/0139996 A1 | | 6/2005 | Myers et al. |
| 2005/0277912 A1 * | | 12/2005 | John ........................ 604/890.1 |
| 2006/0111693 A1 | | 5/2006 | Lautenbach |
| 2007/0190695 A1 | | 8/2007 | Myers et al. |

FOREIGN PATENT DOCUMENTS

WO    WO 2004/054811 A2    7/2004

OTHER PUBLICATIONS

European Search Report for application No. 08168781.6 dated Dec. 22, 2009.

* cited by examiner

*Primary Examiner* — Brian J Sines
(74) *Attorney, Agent, or Firm* — Kermit D. Lopez; Luis M. Ortiz; Kevin Soules

(57) ABSTRACT

A micro-fluidic osmotic pump capable of delivering a desired fluid at a predetermined destination comprising an inside fluid reservoir housing a compressible sac, a surrounding compartment having an external surface made up of a semi-permeable membrane and a fluid duct. The inside fluid reservoir houses a compressible sac containing a predetermined amount of a fluid that is desired to be pumped to a predetermined destination. The surrounding compartment holds a desired osmotic agent and its saturated solution in the remaining volume thereof. The surrounding compartment has an outer surface made up of a semi-permeable membrane that allows a predetermined second external fluid to permeate into the surrounding compartment. The fluid duct is substantially housed within the inside fluid reservoir and runs through openings and respectively provided through the inside fluid reservoir and the surrounding compartment.

2 Claims, 2 Drawing Sheets

MICROFLUIDIC OSMOTIC PUMP

FIELD OF THE INVENTION

The present invention relates to a microfluidic osmotic pump. More particularly, the present invention relates to a microfluidic osmotic pump that is capable of on-chip pumping without any external power input.

BACKGROUND OF THE INVENTION

The current advancements in technology demand that micro-sized devices be used in a variety of applications from medicine to biochemistry. An advantage of the use of these microfluidic devices is that at micro levels, it is much easier to ensure experimental precision because of the laminar flow of fluids at such scales.

These microfluidic devices find application in molecular biology procedures for enzymatic analysis, DNA analysis, proteomics and clinical pathology. All of these high-end applications are based on a continuous flow of a predetermined liquid through microfabricated channels. In the majority of the conventional devices known in the art, the actuation of the liquid flow is normally achieved by the application of external pressure, external mechanical micro-pumping or by electrokinetic pumping effected through the application of a voltage potential. However, there exists a need within the art for an osmotic pump that is capable of microfluidic on-chip pumping without the application of an external pressure or electrokinetic or external mechanical pumping.

These microfluidic devices are suitable for use in a drop-on-demand inkjet printing devices for ejecting printing ink in a suitable manner. These devices usually take the form of an inkjet printhead that is capable of being incorporated within conventional printing devices such as printers, copiers and facsimile machines. However, use of such devices for inkjet printing is exemplary and such devices may find use in other applications wherein small and a controlled amount of fluid ejection on demand is desired.

For example, the microfluidic devices may be used for delivering pharmaceutically beneficial agents in a controlled and regulated manner over a preselected time or administration period. These devices usually comprise a piston with a recess for imbibing an osmotic agent, which actuates the piston to release corresponding amounts of the beneficial agent. However, the use of a piston makes the micro-level fabrication of these devices cumbersome and therefore cost-intensive. Further, the use of a piston reduces the space efficiency of the microfluidic device because the space occupied by the piston compromises either the amount of the osmotic agent, which leads to an insufficient pumping or the amount of the beneficial agent, which is again undesirable.

These devices conventionally comprise a contractible chamber and duct interconnecting a fluid reservoir with a destination. As another example, these microfluidic devices may be used for cooling of electronic devices, wherein the reservoir may contain the cooling agent and the destination is an electronic device that requires cooling. In another application, the fluid reservoir may act as a fuel tank supplying predetermined amount of fuel to a miniature engine. In another application, the reservoir may contain a specimen which may be assayed on an observation slide.

In yet another application, the reservoir may contain a chemical reagent which is fed to a process stream destination enabling a controlled stoichiometric chemical reaction. In another application, the reservoir may contain a colorant which may be fed to a colorant application system. However, it has not been made possible in the current state of the art to provide a microfluidic osmotic pump that is capable of on-chip pumping of a predetermined liquid in a controlled and regulated manner without the application of any external power input.

Numerous attempts have been made in the present state of the art to address these and other problems but none have been found to adequately address the aforesaid requirements.

PCT Publication No. 2004/054811 discloses a microfluidic actuator for ejecting ink through a nozzle comprising a deflectable membrane, an actuator chamber and a nanostructure. The nanostructure deflects towards the membrane upon application of an operating voltage which deflects the membrane causing the ink ejection through the nozzle. The present invention solves the need for a microfluidic osmotic pump which enables on-chip pumping of a fluid without the application of an external voltage field.

US Patent Publication 2005/0070884 A1 discloses an osmotic pump comprising a vent that allows a gradual venting of osmotic material after the drug formulation in the osmotic pump is delivered. It had been observed that subsequent to the delivery of the beneficial agent, the remaining osmotic agent continued to imbibe water from the environment of operation leading to a gradual increase in pressure within the system. With the passage of time, it was seen that due to an incessant gradual increase in pressure, any component of the osmotic pump gets compromised or physically separated. Moreover, the disclosed osmotic pump necessarily includes a piston, which as seen above, reduces the space efficiency of the microfluidic device apart from increasing the fabrication complexity and the associated manufacturing costs thereof.

US Patent Publication 2006/0111693 discloses an osmotic pump having a space efficient piston housed within a capsule. The described piston acts as a movable seal which separates the osmotic agent from the beneficial agent. The finding of the disclosed invention is that a piston having a length to total diameter ratio of about 1.1:1 and a core diameter to total diameter ratio of about 0.9:1 enables greater beneficial agent and/or osmotic agent payload without substantially increasing the size of the payload. However, there is a continuous need in the art to eliminate the use of the pistons in such microfluidic systems to achieve maximum space efficiency of the real-estate within the microfluidic devices.

Thus, there exists a need in the art for a microfluidic osmotic pump that is capable of on-chip pumping of a desired fluid held within without an external power input and which eliminates the use of conventional pistons used within such known devices.

SUMMARY OF THE INVENTION

Accordingly, it is an object of the present invention to provide a microfluidic osmotic pump that is capable of on-chip pumping a desired fluid to a predetermined destination without any external power input.

Another object of the present invention is to provide a microfluidic osmotic pump that is capable of pumping a desired fluid to a predetermined destination in a controlled and regulated manner over a preselected time or administration period.

Yet another object of the present invention is to provide a microfluidic osmotic pump that eliminates the use of a piston thereby enhancing the space efficiency of the osmotic pump without comprising the amount of an osmotic agent or the desired fluid delivered to a predetermined destination.

Another object of the present invention is to provide a microfluidic osmotic pump which utilizes an osmotic agent to drive a desired fluid to a predetermined destination thereby avoiding the use of an external power input.

Another object of the present invention is to provide a microfluidic osmotic pump wherein the pumping rate of the desired fluid is a function of the permeability of a semi-permeable membrane or the characteristics of the osmotic agent and is therefore easily controllable.

Yet another object of the present invention is to provide a microfluidic osmotic pump that is capable of delivering a very low and accurate flow rate of a desired fluid at a predetermined destination.

Accordingly, in one aspect, the present invention provides a microfluidic osmotic pump capable of delivering a desired fluid at a predetermined destination comprising an inside fluid reservoir housing a compressible sac, a surrounding compartment having an external surface made up of a semi-permeable membrane and a fluid duct. The inside fluid reservoir houses a compressible sac containing a predetermined amount of a fluid that is desired to be pumped to a predetermined destination. The surrounding compartment holds a desired osmotic agent and its saturated solution in the remaining volume thereof. The surrounding compartment has an outer surface made up of a semi-permeable membrane that allows a predetermined second external fluid to permeate into the surrounding compartment but is substantially impermeable to the osmotic agent held within the surrounding compartment. The fluid duct is substantially housed within the inside fluid reservoir and runs through openings provided through the inside fluid reservoir and the surrounding compartment. The fluid duct has a first end immersed in the desired fluid held within the inside fluid reservoir and a second end protruding out of the microfluidic osmotic pump. During the operation of the microscopic osmotic pump, it is exposed to a predetermined external fluid. The semi-permeable membrane outer surface of the surrounding compartment allows the external fluid to permeate into the surrounding compartment and solvate the osmotic agent contained within the surrounding compartment to a resulting solvated osmotic agent. The solvated osmotic agent thus produced is dissolved into the saturated solution held within the surrounding compartment thereby developing an osmotic pressure. The osmotic pressure thus developed compresses the compressible sac housed within the inside fluid reservoir to pump out the fluid held within the sac through the fluid duct.

BRIEF DESCRIPTION OF THE DRAWINGS

The invention will now be described in connection with the drawing described hereinafter.

DETAILED DESCRIPTION OF THE INVENTION

In accordance with an exemplary embodiment of the invention, there is provided a microfluidic osmotic pump capable of delivering a desired fluid at a predetermined destination comprising: an inside fluid reservoir adapted to contain a predetermined amount of a first desired fluid within a compressible sac housed within said inside fluid reservoir; a surrounding compartment that houses said fluid reservoir and is adapted to hold a desired osmotic agent and its saturated solution in a desired second external fluid in the remaining volume thereof; said surrounding compartment having an outer surface made up of a semi-permeable membrane that allows said predetermined second external fluid to permeate through the semi-permeable membrane into said surrounding compartment but is substantially impermeable to said osmotic agent held within said surrounding compartment; and a fluid duct substantially housed within said inside fluid reservoir that runs through openings provided through said inside fluid reservoir and said surrounding compartment, said fluid duct having a first end immersed in the desired fluid held within said inside fluid reservoir and a second end protruding out of the microfluidic osmotic pump.

Figure 1:
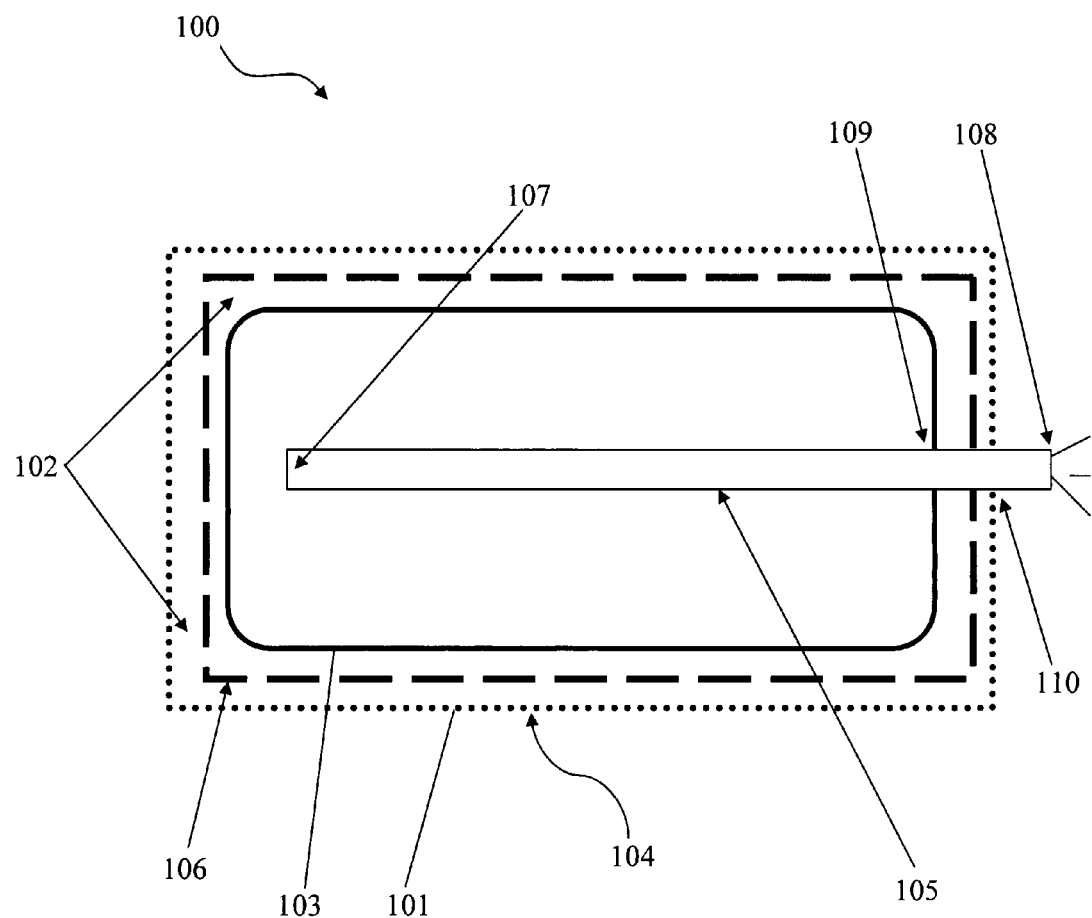
FIG. 1 illustrates a microfluidic osmotic pump in accordance with the present invention.

Referring to FIG. 1, illustrated is a microfluidic osmotic pump 100 capable of delivering a desired fluid at a predetermined destination comprising an inside fluid reservoir 102 housing a compressible sac 103, a surrounding compartment 101 having an external surface 104 made up of a semi-permeable membrane and a fluid duct 105. The inside fluid reservoir 102 houses a compressible sac 103 containing a predetermined amount of a fluid (not shown) that is desired to be pumped to a predetermined destination (not shown). The surrounding compartment 101 holds a desired osmotic agent 106 and its saturated solution in the volume remaining between the surrounding compartment and the compressible sac 103. The surrounding compartment 101 has an outer surface made up of a semi-permeable membrane that allows a predetermined external fluid (not shown) to permeate into the surrounding compartment but is substantially impermeable to the osmotic agent 106 held within the surrounding compartment. The fluid duct 105 is substantially housed within the inside the compressible sac 103 held within the fluid reservoir 102 and enables a desired fluid (not shown) held within the compressible sac 103 to run through openings 107 and out through 108 to a predetermined destination. The desired fluid flows from the compressible sac 103 when pressure is formed within the fluid reservoir 102 formed inside the surrounding compartment 101. The fluid duct 105 is attached as shown at location 109 with the compressible sac 103 and has a first end 107 immersed in the desired fluid held within the compressible sac 102 and a second end 108 protruding out of the surrounding compartment 101 defining an outer housing of microfluidic osmotic pump. The fluid duct 105 is sealed at its location of attachment 110 and exit point through the surrounding compartment 101.

During the operation of the microscopic osmotic pump, it is exposed to a predetermined external fluid. The semi-permeable membrane of the outer surface of the surrounding compartment allows the external fluid to permeate into the surrounding compartment and solvate the osmotic agent contained within the surrounding compartment to a resulting solvated osmotic agent. The solvated osmotic agent thus produced is dissolved into the saturated solution held within the surrounding compartment thereby developing an osmotic pressure. The osmotic pressure thus developed compresses the compressible sac housed within the inside fluid reservoir to pump out the fluid held within the sac through the fluid duct.

Figure 2:
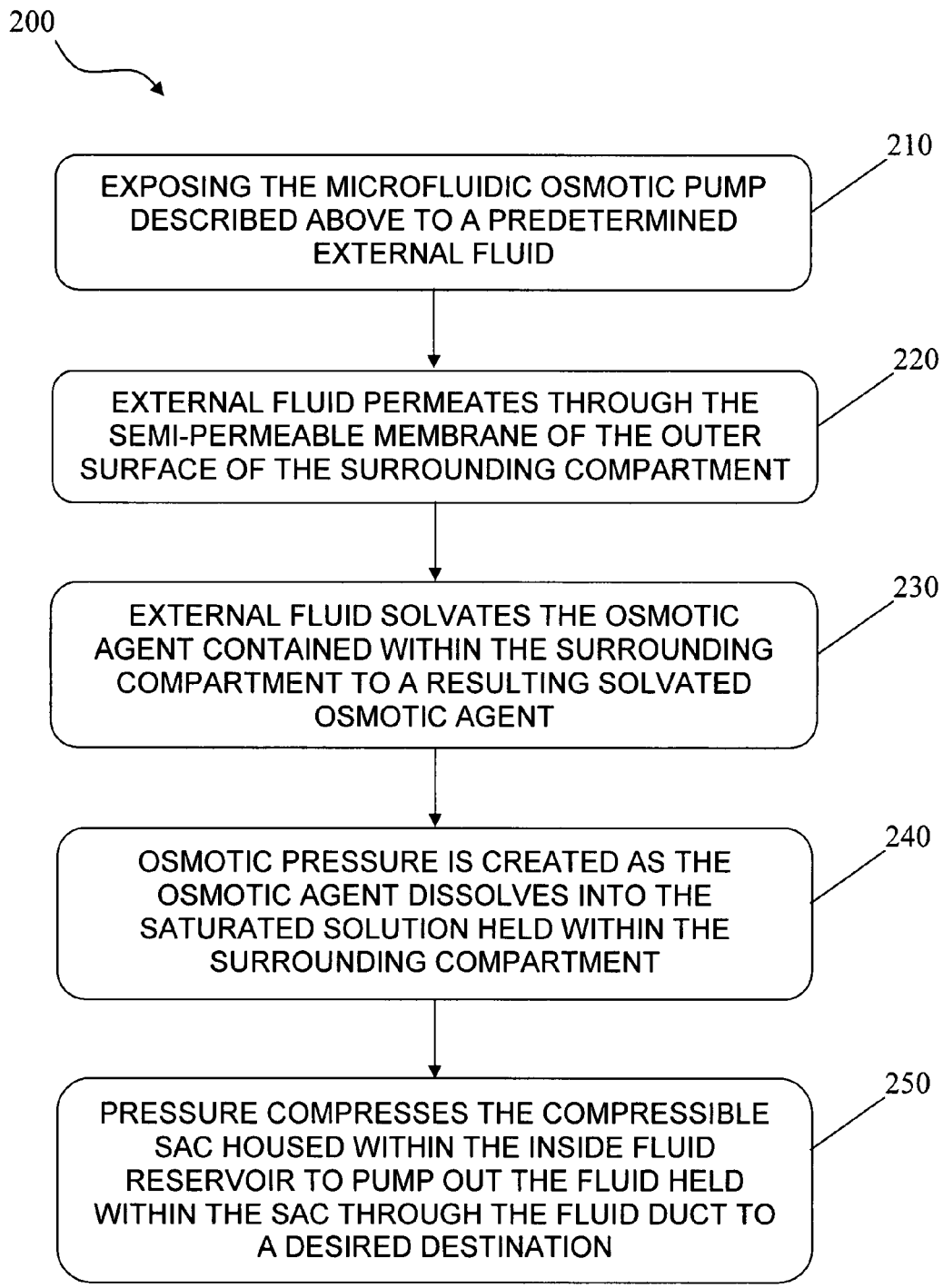
FIG. 2 illustrates a method utilizing a microfluidic osmotic pump in accordance with the present invention.

In another aspect, the present invention further provides a method for delivering a desired fluid at a predetermined destination. Referring to FIG. 2, the method begins by exposing the microfluidic osmotic pump described above to a predetermined external fluid as shown in Block 210. The external fluid permeates through the semi-permeable membrane of the outer surface of the surrounding compartment as shown in Block 120, and the external fluid solvates the osmotic agent contained within the surrounding compartment to a resulting solvated osmotic agent as shown in Block 130. An osmotic pressure is created as the osmotic agent dissolves into the saturated solution held within the surrounding compartment as shown in Block 140. The pressure compresses the compressible sac housed within the inside fluid reservoir to pump out the fluid held within the sac through the fluid duct to a desired destination as shown in Block 150.

It has thus been made possible to use the osmotic force to pump a desired fluid to a predetermined destination without the need for applying an external power input.

In a preferred embodiment, the outer surface of the surrounding compartment composed of a semi-permeable membrane allows only water to permeate inside the surrounding compartment, where it comes into contact with the osmotic agent to form hydrated osmotic agent. The hydrated osmotic agent goes into the saturated solution of the osmotic agent in water, which was previously housed within the surrounding compartment. The saturated solution does not imbibe the osmotic agent before its hydration though being housed within the same surrounding compartment due to its saturation, which prevents it from dissolving further solute without being hydrated. The dissolution of the hydrated osmotic agent develops an osmotic pressure which compresses the compressible sac inside the fluid reservoir thereby providing the necessary force to pump the fluid contained within the sac to any predetermined destination.

It has been seen that the dissolution of the hydrated osmotic agent in its saturated solution develops an osmotic pressure of the order of several hundreds of pounds per square inches.

It has further been found that the pumping rate of the desired fluid is a function of the osmotic agent and water permeability of the semi-permeable membrane. It has been seen that a greater water permeability of the semi-permeable membrane results in a higher pumping rate of a desired fluid.

It has further been found that the microfluidic osmotic pump of the present invention is capable of delivering a very low and accurate flow rate that is desirable in many applications. For example, it has been made possible to attain flow rates of the desired fluid from 2 to 150 nL/min by varying the parameters such as the choice of the osmotic agent, water permeability of the chosen semi-permeable membrane and the choice of the solvating fluid. It was further found that at a flow rate of 150 nL/min, a 0.9 mL of a desired fluid was pumped in a controlled manner over a time period of 100 hours of continuous operation.

In a preferred embodiment, the osmotic agent is selected from a group consisting of NaCl, KCl, MgSO4 and mixture of them.

In another preferred embodiment, the semi-permeable membrane is selected from a group consisting of cellulose acetate, PTFE, and polyvinylacetate (PVAC). Typical permeability values of the semi-permeable membranes found suitable for use in the osmotic pumps of the present invention varied from $4.5 \times 10_{-2}$ μl mm/(s mm$_2$ Pa) to $4.5 \times 10_{-7}$ μl mm/(s mm$_2$ Pa).

It has been found that the osmotic pump of the present invention is capable of being embedded into a microfluidic chip of credit card like dimensions to facilitate active on chip pumping, which finds use in a variety of non-limiting applications such as those described hereinabove under the background.

For example, the microfluidic osmotic pump of the present invention may find application as the inkjet head for drop-on-demand inkjet printing or may be used in systems requiring precise control of fluid delivery through a chip such as those in biosciences or nano-chemistry.

It will be understood that the figure and description of the present invention has been simplified to illustrate elements that are relevant for a clear understanding of the present invention, while eliminating, for the purpose of clarity, many other elements that occur in microfluidic devices known in the art. Those of ordinary skill in the art will recognize that other elements are desirable in implementing the present invention. However, because such elements are well known in the art and they do not facilitate a better understanding of the present invention, a discussion of such elements has not been provided herein.

For example, the microfluidic osmotic pumps of the present invention may be embedded on a microfluidic transmitter through a batch process, which allows seamless interfacing of microfluidic pumping with light emitting chemistry. In this preferred embodiment of the microfluidic osmotic pump, the inside fluid reservoir is loaded with a pusher fluid, which is immiscible with another chemiluminescence fluid. The osmotic pumps of the present invention may thereafter be integrated with a microfluidic circuit wherein the pusher fluid that provides the shearing source and the continuous phase that carries an intermittent slug to be delivered through a barcode window. The microfluidic osmotic pumps of the present invention may be embedded on a microfluidic transmitter using methods that are conventionally known in the art including lamination and injection molding.

It has now been made possible to embed an osmotic pump onto a laminated card of credit card size having a thickness of about 1 cm. The embedded card may be designed and fabricated for use as an off-the-shelf osmotic pump, whose performance may be accurately predicted and experimentally verified.

In another embodiment, the osmotic pump may be fabricated on a flat card size substrate using methods such as dry powder deposition, membrane lamination, blister packaging and multilayer lamination technology. The card sized substrate may thereafter be readily inserted into a plastic cartridge for printing use.

These microfluidic osmotic pumps may find application in molecular biology procedures for enzymatic analysis, DNA analysis, proteomics and clinical pathology. For example, the microfluidic osmotic pumps according to the present invention may be used for delivering pharmaceutically beneficial agents in a controlled and regulated manner over a preselected time or administration period. The beneficial agent may be housed within the described inside fluid reservoir. Upon imbibition of the gastric juices and other external fluids depending upon the release site, the osmotic pump may be actuated to release controlled amounts of the beneficial agent over a predetermined administration period for a controlled and regulated delivery of the beneficial agent.

In yet another application, the microfluidic osmotic pumps according to the present invention may be used for cooling electronic devices, wherein the inside fluid reservoir may contain the cooling agent and the desired destination for delivering the cooling agent may be an electronic device that requires cooling.

In another application, the inside fluid reservoir may act as a fuel tank supplying predetermined amount of fuel to a miniature engine.

In another application, the reservoir may contain a specimen which may be assayed on an observation slide.

In yet another application, the inside fluid reservoir may contain a chemical reagent, which is fed to a process stream destination enabling a controlled stoichiometric chemical reaction.

In another application, the reservoir may contain a colorant which may be fed to a colorant application system.

Those of ordinary skill in the art will recognize that many modifications and variations of the present invention may be implemented without departing from the spirit or scope of the invention. Thus, it is intended that the present invention covers the modifications and variations of this inventions within come within the scope of the appended claims and their equivalents.

What is claimed is:

1. A method for delivering a desired fluid at a predetermined destination, said method comprising:

providing a microfluidic osmotic pump including a surrounding compartment wherein an external surface of said surrounding compartment comprises a semi-permeable membrane, an osmotic agent contained within a fluid reservoir formed within the surrounding compartment, a compressible sac disposed within the fluid reservoir, and a fluid duct coupled to said compressible sac and ported through said surrounding compartment;

exposing a microfluidic osmotic pump to a predetermined external fluid, wherein said predetermined external fluid permeates through said semi-permeable membrane;

solvating said predetermined external fluid with said osmotic agent contained within the surrounding compartment resulting in a production of solvated osmotic agent; and developing an osmotic pressure within said surrounding compartment as said solvated osmotic agent is produced, wherein said pressure compresses said compressible sac housed within the fluid reservoir to pump out secondary fluid held within the compressible sac through said fluid duct to a desired destination; and pumping fluid out of said compressible sac as pressure is developed within said reservoir.

2. The method for delivering a desired fluid at a predetermined destination as claimed in claim 1, wherein said compressible sac housed within said fluid reservoir contains said secondary fluid comprising a pusher fluid and the desired destination is a housing associated with a microfluidic circuit containing a chemiluminescence fluid.

* * * * *